United States Patent
Sola i Caros et al.

(10) Patent No.: US 10,165,951 B2
(45) Date of Patent: Jan. 1, 2019

(54) SENSOR DEVICE AND METHOD FOR MEASURING AND DETERMINING A PULSE ARRIVAL TIME (PAT) VALUE

(71) Applicant: CSEM CENTRE SUISSE D'ELECTRONIQUE ET DE MICROTECHNIQUE SA—RECHERCHE ET DÉVELOPPEMENT, Neuchatel (CH)

(72) Inventors: Josep Sola i Caros, Neuchatel (CH); Stefano Rimoldi, Solothurn (CH)

(73) Assignee: CSEM CENTRE SUISSE D'ELECTRONIQUE ET DE MICROTECHNIQUE SA—RECHERCHE ET DÉVELOPPEMENT, Neuchatel (CH)

( * ) Notice: Subject to any disclaimer, the term of this patent is extended or adjusted under 35 U.S.C. 154(b) by 873 days.

(21) Appl. No.: 13/629,673

(22) Filed: Sep. 28, 2012

(65) Prior Publication Data
US 2013/0041268 A1    Feb. 14, 2013

Related U.S. Application Data

(63) Continuation of application No. PCT/EP2011/054834, filed on Mar. 29, 2011.
(Continued)

(51) Int. Cl.
*A61B 5/021* (2006.01)
*A61B 5/024* (2006.01)
(Continued)

(52) U.S. Cl.
CPC ............ *A61B 5/021* (2013.01); *A61B 5/0285* (2013.01); *A61B 5/0295* (2013.01);
(Continued)

(58) Field of Classification Search
None
See application file for complete search history.

(56) References Cited

U.S. PATENT DOCUMENTS 6,331,162 B1 * 12/2001 Mitchell .................. 600/485
6,714,804 B2 * 3/2004 Al-Ali ................ A61B 5/746
                                                        600/323
(Continued)

OTHER PUBLICATIONS

Hodge et al. ("A survey of Outlier Detection Methodologies"; Klvwer Academic Publishers; Jan. 19, 2004).*
(Continued)

*Primary Examiner* — Michael Kahelin
*Assistant Examiner* — Shahdeep Mohammed
(74) *Attorney, Agent, or Firm* — Pearne & Gordon LLP

(57) ABSTRACT

A method for measuring and determining a pulse arrival time (PAT) value of a user using a sensor device having a photoplethysmographic (PPG) multichannel sensor formed from a plurality of PPG sensor channels and being adapted to measure a set of PPG signals, each PPG signal being measured by one of the PPG sensor channels when the multichannel PPG sensor is in contact with the user; having: measuring the set of PPG signals; extracting a plurality of features from each of the measured PPG signals; selecting a subset from the set of PPG signals based on the extracted features; and processing the selected subset of PPG signals to determine the PAT value. The disclosed sensor and method can be embedded into a chest belt and do not need skilled supervision. They can represent a potential candidate for the implantation of PWV measurement campaigns in the ambulatory setting.

16 Claims, 7 Drawing Sheets

Related U.S. Application Data

(60) Provisional application No. 61/318,444, filed on Mar. 29, 2010.

(51) Int. Cl.
*A61B 5/0285* (2006.01)
*A61B 5/0452* (2006.01)
*A61B 5/00* (2006.01)
*A61B 5/0295* (2006.01)

(52) U.S. Cl.
CPC ...... *A61B 5/02125* (2013.01); *A61B 5/02416* (2013.01); *A61B 5/0452* (2013.01); *A61B 5/6831* (2013.01); *A61B 5/721* (2013.01); *A61B 5/7239* (2013.01); *A61B 2562/0233* (2013.01); *A61B 2562/046* (2013.01)

(56) References Cited

U.S. PATENT DOCUMENTS

| | | | | |
|---|---|---|---|---|
| 6,805,673 | B2* | 10/2004 | Dekker | A61B 5/0205 600/324 |
| 7,034,738 | B1* | 4/2006 | Wang et al. | 342/13 |
| 7,397,415 | B1* | 7/2008 | Wang et al. | 342/13 |
| 8,386,000 | B2* | 2/2013 | McKenna | A61B 5/14551 600/310 |
| 2007/0276261 | A1* | 11/2007 | Banet et al. | 600/481 |
| 2008/0234598 | A1* | 9/2008 | Snyder et al. | 600/545 |
| 2009/0281399 | A1* | 11/2009 | Keel | A61B 5/02158 600/301 |
| 2009/0292217 | A1* | 11/2009 | Bartnik et al. | 600/523 |
| 2010/0081946 | A1* | 4/2010 | Garudadri | A61B 5/0002 600/485 |
| 2010/0331640 | A1* | 12/2010 | Medina | A61B 5/14535 600/324 |
| 2011/0040345 | A1* | 2/2011 | Wenzel et al. | 607/17 |
| 2011/0144456 | A1* | 6/2011 | Muhlsteff | A61B 5/02125 600/301 |
| 2012/0190948 | A1* | 7/2012 | Vetter | A61B 5/02405 600/324 |
| 2013/0023776 | A1* | 1/2013 | Olde et al. | 600/487 |

OTHER PUBLICATIONS

Josep Sola et al: "Parametric estimation of pulse arrival time: a robust approach to pulse wave velocity", published Jul. 1, 2009 in Physiological Measurement, Institute of Physics Publishing, Bristol, GB, vol. 30, No. 7, pp. 603-615.

Josep Sola et al: "Chest Pulse-Wave Velocity: A Novel Approach to Assess Arterial Stiffness", published Jan. 1, 2011 in IEEE Transactions on Biomedical Engineering, IEEE Service Center, Piscataway, NJ, USA, vol. 58, No. 1 pp. 215-223.

Josep Sola et al: "Ambulatory monitoring of the cardiovascular system: the role of Pulse Wave Velocity", published Jan. 1, 2010 in New Developments in Biomedical Engineering, Intech, pp. 391-424.

R. Vetter et al: "Frequency domain Sp02 Estimation Based on Multichannel Photoplethysmographic Measurements at the Sternum", published Jan. 1, 2009 in IFMBE Proceedings (International Federation for Medical and Biological Engineering) Springer, DE, vol. 25, No. 4, pp. 326-329.

International Search Report dated Jul. 6, 2011 for application No. PCT/EP2011/054834.

* cited by examiner (a)

(b)

SENSOR DEVICE AND METHOD FOR MEASURING AND DETERMINING A PULSE ARRIVAL TIME (PAT) VALUE

FIELD

The present invention concerns a sensor device using a photoplethysmographic (PPG) sensor and a method for measuring and determining a pulse arrival time (PAT) value of a user.

BACKGROUND

Pulse wave velocity (PWV) represents the velocity at which pressure pulses propagate through the arterial tree. PWV is considered as the gold standard measurement to assess arterial stiffness, and has been identified as an independent predictor of cardiovascular morbidity and mortality. In line with this data, in 2007 the European Society of Hypertension has introduced PWV as a recommended test to assess cardiovascular risk on its guidelines for the diagnosis and management of hypertension.

Nowadays techniques that allow assessing PWV non-invasively fall into two main categories. On the one hand, COMPLIOR (Colson, France), SphygmoCor (AtCor Medical, Australia), Vicorder (Skidmore Medical, UK) and PulsePen (Diatecne, Italy) rely on the placement of two pressure transducers onto two superficial arteries. These devices detect the arrival time of a pressure pulse that propagates through the arterial tree, and calculate the delay in pulse arrival times between the proximal and distal sensors. By approximately measuring the distance through which the pulse has propagated, one estimates then a pulse propagation velocity value. Large clinical studies support the reliability and clinical validity of this technique.

On the other hand, Arteriograph (TensioMed, Hungary) estimates aortic PWV by applying pulse wave analysis techniques to a pressure pulse recorded by an inflated brachial cuff. The major interest of this approach is that PWV measurements can be performed automatically, reducing the need of trained medical staff. The measurement is based on the fact that during systole, the blood volume having been ejected into the aorta generates a pressure pulse (early systolic peak). This pulse runs down and reflects from the bifurcation of the aorta, creating a second pulse (late systolic peak). The return time (RT S35) is the difference between the first and the second systolic pulse waves, and is claimed to be a surrogate of aortic PWV. Unfortunately, clinical and numerical studies currently question the reliability and working principles of the RT S35 technique.

A broader review on the technical and physiological background of the described techniques is provided in J. Solà, S. F. Rimoldi, and Y. Allemann, "Ambulatory monitoring of the cardiovascular system: the role of Pulse Wave Velocity", in *New Developments in Biomedical Engineering*, Intech, 2010 (Ref. 1). Because COMPLIOR-like devices are the state of the art of non-invasive measurement of arterial stiffness, a new implemented technique that would reduce the need of trained medical staff is highly desired. This would have the advantage of being operator dependent, and thus would facilitate the introduction of PWV measurements in large scale ambulatory and follow-up studies.

SUMMARY

The present application discloses a sensor device and a method for measuring and determining a pulse arrival time (PAT) value of a user which overcome at least some limitations of the prior art.

The present disclosure concerns a method for measuring and determining a pulse arrival time (PAT) value of a user using a sensor device comprising a photoplethysmographic (PPG) multichannel sensor formed from a plurality of PPG sensor channels and being adapted to measure a set of PPG signals, each PPG signal being measured by one of the PPG sensor channels when the multichannel PPG sensor is in contact with the user; comprising:
  measuring said set of PPG signals;
  extracting a plurality of features from each of the measured PPG signals;
  selecting a subset from the set of PPG signals based on the extracted features; and
  processing the selected subset of PPG signals to determine the PAT value.

In an embodiment, said extracting a plurality of features can comprise fitting a parametric model to each PPG signal of said set of PPG signals, the features corresponding to the parameters of the fitted model.

In another embodiment, said selecting a subset of PPG signals can comprise:
  projecting the plurality of features extracted from each of the measured PPG signal into a set of points in a N-dimensional feature space where N corresponds to the number of extracted features for each PPG signal;
  clustering the set of points according to a distance criterion; and
  selecting points being located at the most representative cluster, the selected points corresponding to the subset of PPG signals.

In yet another embodiment, said clustering the set of points can comprise:
  calculating a representative point;
  calculating a distance for the set of points to the representative point; and
  clustering together those points being located at a distance smaller than a distance threshold.

In yet another embodiment, said calculating a representative point can comprise calculating the median point of the set of points.

In yet another embodiment, said calculating a distance for the set of points can comprise calculating a Mahalanobis distance.

In yet another embodiment, said distance threshold can be calculated from a histogram of the distances for the set of points to the representative point.

In yet another embodiment, said processing the selected subset of PPG signals can comprise estimating a representative value of at least one of the features extracted from each of the selected subset of PPG signals.

In yet another embodiment, the sensor device further comprises an electrocardiography (ECG) sensor for measuring an ECG signal, an impedance cardiography (ICG) sensor for measuring an ICG signal, and a phonocardiography (PCG) sensor for measuring a PCG signal; and the method can further comprise:
  measuring the ECG signal with the ECG sensor such as to detect a R-Wave corresponding to the onset of left-ventricular depolarization,
  triggering the PCG signal measured by the PCG sensor and the ICG signal measured by the ICG sensor by the detected R-Wave;
  performing an ensemble average of the triggered PCG signal and ICG signal;
  calculating the maximum of the envelope of the ensemble-averaged PCG signal; and detecting a maximum of the third derivative of the ensemble-averaged ICG signal being closest to the maximum of the envelope such as to determine a value of a pre-ejection period (PEP).

In yet another embodiment, the determined value of the pre-ejection period (PEP) is being used in combination with the determined PAT value to estimate a pulse transit time (PTT) value.

In yet another embodiment, the method can further comprise estimating a pulse wave velocity (PWV) value by dividing the estimated PTT value by a measured distance of the user's body.

In yet another embodiment, the method can further comprise calculating a blood pressure value from the estimated PTT value by measuring reference blood pressure values using a brachial cuff, and calibrating PTT values according to measured reference blood pressure values.

In yet another embodiment, the method can further comprise calculating a blood pressure value from the estimated PWV value by measuring reference blood pressure values using a brachial cuff, and calibrating PWV values according to measured reference blood pressure values.

The present disclosure also pertains to a sensor device comprising a photoplethysmographic (PPG) multichannel sensor formed from a plurality of PPG sensor channels and being adapted to measure a set of PPG signals, each PPG signal being measured by one of the PPG sensor channels when the multichannel PPG sensor is in contact with the user, wherein the PAT value can be determined using the method disclosed herein.

In an embodiment, the sensor device can further comprise an impedance cardiography (ICG) sensor for measuring an ICG signal, an electrocardiography (ECG) sensor for measuring an ECG signal, and a phonocardiography (PCG) sensor for measuring a PCG signal; the ICG sensor, ECG sensor, and PCG sensor being used in combination for determining a value of a pre-ejection period (PEP) using the method disclosed herein.

The method is able to assess central pulse wave velocity (PWV) continuously in a fully unsupervised manner has been presented. A 20-subject in-vivo study has shown that chest PWV highly correlates with the COMPLIOR carotid to radial PWV measurement. In conclusion, chest PWV appears to be a consistent method to continuously estimate PWV of central elastic and large muscular arteries in the ambulatory setting.

The present application provides evidence for a potential novel technique that assesses PWV along a vascular tree including both central elastic and peripheral non-elastic arteries, and that is prone to be integrated in a chest belt sensor. Comparison to COMPLIOR carotid to radial and COMPLIOR carotid to femoral PWV measurements is provided.

The disclosed sensor and method can be embedded into a chest belt and do not need skilled supervision. They can represent a potential candidate for the implantation of PWV measurement campaigns in the ambulatory setting.

BRIEF DESCRIPTION OF THE DRAWINGS

The preferred embodiments will be better understood with the aid of the description of an embodiment given by way of example and illustrated by the figures, in which.

DETAILED DESCRIPTION OF POSSIBLE EMBODIMENTS

Arterial pressure pulses are generated at the onset of left-ventricular ejection: after an initial period of isovolumetric contraction, the ventricular pressure exceeds arterial pressure and forces the aortic valve to open. The sudden rise of aortic pressure distends the elastic walls of the ascending aorta, thus creating a pressure pulse that propagates through the walls of the entire arterial tree. Of particular interest in the context of this paper is the pressure pulse traveling from the aortic valve (proximal site) to the capillary bed over the sternum surface (distal site).

After leaving the left ventricle, the pressure pulse propagates through the aorta and moves forward to the brachiocephalic trunk. Up to this point, the propagation is performed through elastic arteries only, at relatively low velocities. From the brachiocephalic trunk the pressure pulse accelerates while propagating through the internal thoracic artery, a large muscular artery, similar to the radial artery, before reaching the heterogeneous capillary bed surrounding the sternum manubrium. Note that because the propagation through the capillary bed is performed at high velocities (Moens-Korteweg equation applied to capillary geometry), the influence of capillary autoregulation to the total transit time can be neglected. Hence, assuming typical propagation velocities and lengths for the described arterial segments, one estimates a pressure pulse to travel 85% of the time through elastic arteries and 15% of the time through muscular arteries and capillaries. Therefore, a pulse wave velocity (PWV) value determination performed at the chest is expected to contain a mixture of elastic and muscular arterial information only, similar to the COMPLIOR carotid to radial PWV parameter.

Figure 1A:
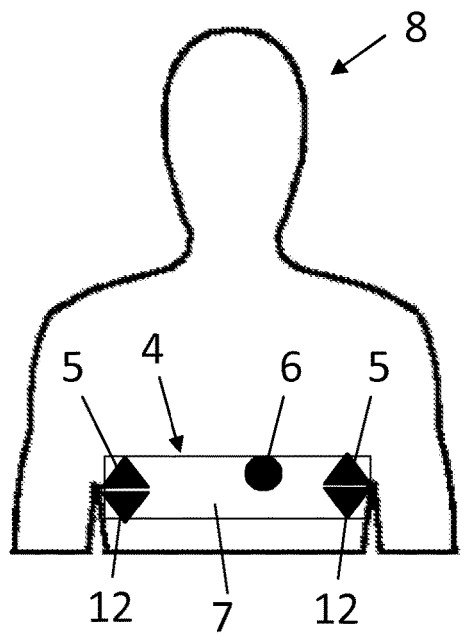
FIGS. 1(a)-(d) illustrate an ICG sensor and PCG sensor placed on a belt worn by a user, and two examples of PCG-guided ICG analysis.
Figure 1B:
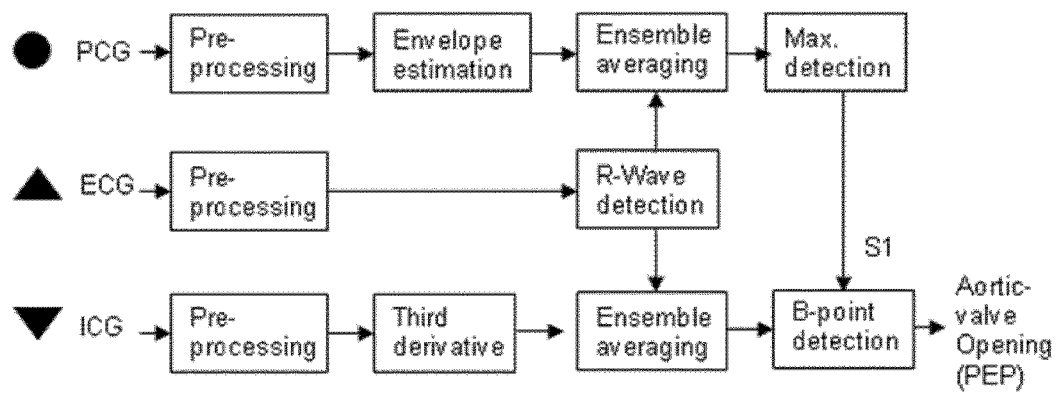
Figure 1C:
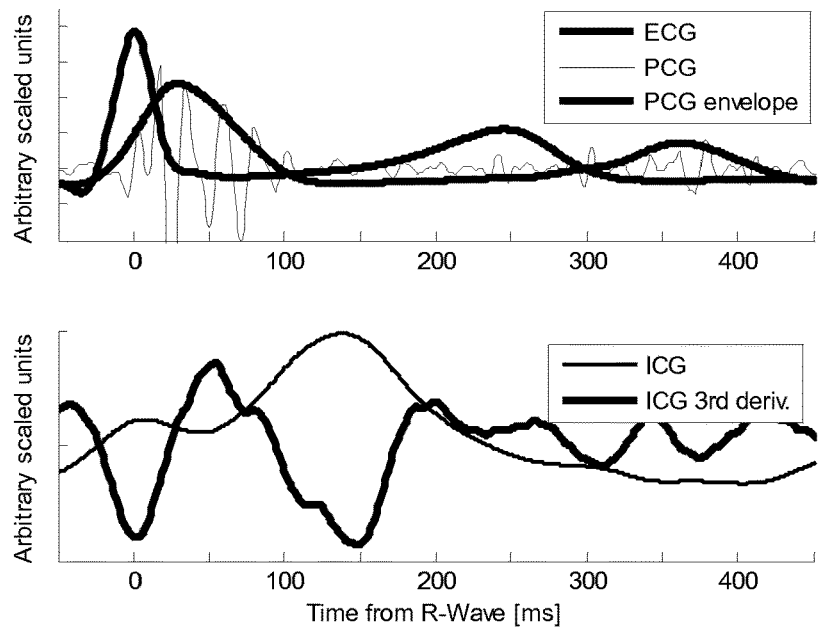
Figure 1D:
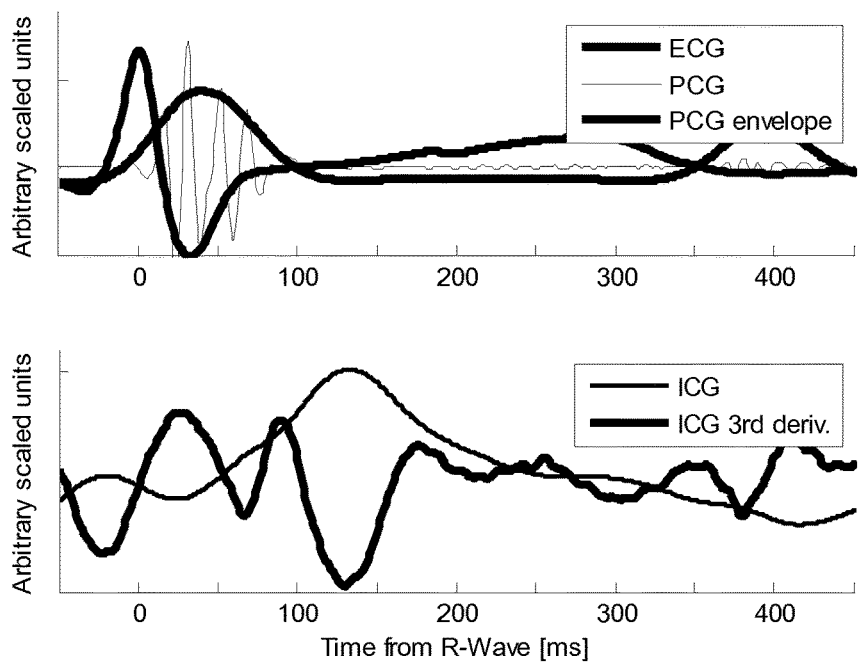
Figure 3A:
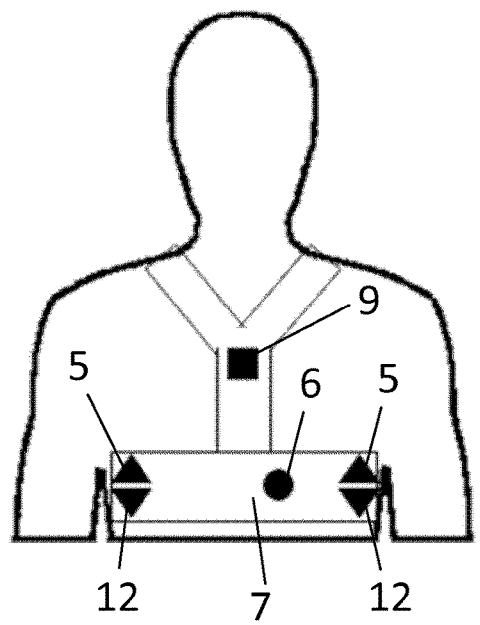
FIGS. 3(a)-(b) illustrate a preferred embodiment where the PPG multichannel sensor is placed on the chest of the user, and a diagram representing the combination of the sensor signals according to an embodiment.
Figure 3B:
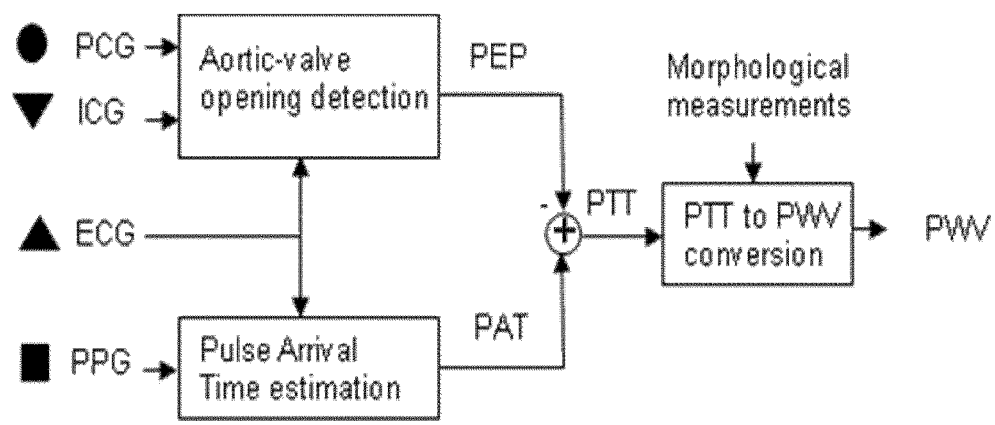

In an embodiment, proposed sensor device, here a sensor device 4 (see FIGS. 1(a) and 3), comprises an electrocardiography (ECG) sensor 12 for measuring an ECG signal, a phonocardiography (PCG) sensor 6 for measuring a PCG signal, and an impedance cardiography (ICG) sensor 5 for measuring an ICG signal, that can be used for example for the detection of the aortic valve opening. The sensor device 4 also comprises a photoplethysmography (PPG) multichannel sensor 9 (see FIG. 3(a)). The PPG multichannel sensor 9 and the ECG sensor 12 can be used in combination for the detection of distal pulse arrival times. In the FIGS. 1(a) and 3(a), the ECG, ICG, PCG and PPG are shown disposed on a belt 7 worn by a user 8.

Although the examples of FIGS. 1(a) and 3(a) represent the sensor device 4 mounted on the belt 7 and being substantially in contact with the chest region of the user, this configuration should however not be seen as a limitation of the sensor device location. Indeed, the sensor device 4 could also be located to any other practical location of the user's body, for example, on the forehead, ear, nose, etc.

Impedance cardiography (ICG) is a well-established technique to non-invasively assess cardiac events and other hemodynamic variables such as pre-ejection period (PEP), and cardiac output. An example of an ICG-based device is the recently FDA-cleared device BioZ DX (Sonosite, USA). ICG relies on the analysis of voltage signals resulting from currents injected through the thorax. A typical ICG sensor setup requires placing four electrodes around the thorax: two current injection electrodes and two voltage measurement electrodes. When detectable, the onset of the rapidly increasing slope of the first derivative of the ICG signal is considered to be a good estimate of the opening of the aortic valve, and is referred to as B-point. However, the wide range of physiological variability of ICG patterns through different subjects and hemodynamic status turns the apparently straightforward identification of B-point to be a critical task. In T. T. Debski, Y. Zhang, J. R. Jennings, and T. W. Kamarck, "Stability of cardiac impedance measures: Aortic opening (B-point) detection and scoring," *Biol. Physchology*, vol. 23, pp. 63-74, 1993, an improved method based on the analysis of the third derivative of the ICG was proposed. This method allows locating B-points even when no inflections are present in the ICG signals. Unfortunately, the third derivative of ICG contains several misleading local maxima, and this approach is hard to be implemented in a fully unsupervised manner.

Phonocardiography (PCG) is a computerized approach to the traditional auscultation of heart sounds. When placing an electronic stethoscope on the chest, one obtains a series of electrical signals containing representative patterns of the first and second heart sounds. In particular the first heart sound of the PCG (S1) is associated to the closure of the tricuspid and mitral valves, preceding the opening of the aortic valve. Although the accurate determination of S1 requires complex signal processing techniques, the maximum of the PCG envelope has been shown to be already a rough estimate of S1.

For the sensor device 4, a joint analysis of PCG and ICG is proposed in D. Bartnik and B. Reynolds, "Impedance Cardiography System and Method," US Patent Application, US 2009/0292217 A1, 2009, for the detection of the aortic valve opening (see FIG. 1(b)). The present approach exploits the robustness of PCG-based techniques and the precision of ICG third-derivative-based techniques. Initially, the R-Wave at the ECG triggers the onset of left-ventricular depolarization. Then, a maximum of the PCG envelope is detected (S1), roughly indicating the onset of left-ventricular ejection. Similarly, in the neighborhood of S1, a maximum of the third derivative of the ICG is expected to be encountered, accurately designating the opening of the aortic valve (B-point). Thus, the proposed approach introduces S1 as an a-priori estimate of the opening of aortic valve, guiding the identification of the B-point at the ICG. Two examples PCG-guided ICG analysis are illustrated in FIG. 1. More particularly, FIG. 1 represents the ICG sensor 5 and PCG sensor 6 placed on the belt 7 worn by the user 8. The user can be a human or an animal. In graph shown in FIG. 1(c), a single maximum of the ICG third derivative (lower graph of FIG. 1(c), dashed line) is present: no a-priori information is needed. In lower graph shown in Fig. (d), two local maxima of the ICG third derivative exist, and the a-priori window defined by the PCG guides the B-point detection, constraining the ICG analysis to a unique solution. The method relies on the detection of the B-point at the third derivative of the impedance cardiograph (ICG).

In an embodiment, a value of the pre-ejection period (PEP) is determined using the sensor device 4, by a method comprising:

measuring the ECG signal with the ECG sensor 12 such as to detect a R-Wave corresponding to the onset of left-ventricular depolarization, triggering the PCG signal measured by the PCG sensor 6 and the ICG signal measured by the ICG sensor 5 by the detected R-Wave;

performing an ensemble average of the triggered PCG signal and ICG signal;

calculating the maximum of the envelope (S1) of the ensemble-averaged PCG signal; and detecting the maximum of the third derivative of the ensemble-averaged ICG signal being closest to the maximum of the envelope (S1).

The maximum of the third derivative of the ensemble-averaged ICG signal being closest to the maximum of the envelope (S1) corresponds to the opening of the aortic valve (B-point) and thus, can be used to determine the pre-ejection period (PEP).

The arrival of a pressure pulse at the sternum manubrium is characterized by a fast and heterogeneous spread of the pulsatile energy through its capillary bed. Reflective photoplethysmography (PPG) is a non-invasive technique that allows detecting the arrival of these pressure pulses. In the examples of FIGS. 1(a) and 3(a), when illuminating the chest region with infrared light, the sternum reflects part of the injected photons. A photodiode in contact with the skin receives then a portion of the reflected energy, containing information on the pulsatility of the illuminated tissues. Unfortunately, PPG signals are severely affected by the heterogeneous distribution of the underlying capillary bed, and the probability that a single PPG sensor illuminates a low-irrigated portion of tissue is non-negligible. Moreover, the low perfusion encountered at the chest, and at other possible user's locations such as forehead, ear and nose, implies PPG signals with signal-to-noise ratios (SNR) lower than −3 dB. In this study a multi-dimensional parametric estimation of pulse arrival times (PAT) is proposed to cope with these difficulties.

Perfusion heterogeneity is managed by introducing spatial diversity (multi-dimensional PAT estimation), and low perfusion by applying noise-robust PAT estimation techniques. In J. Solà, R. Vetter, Ph. Renevey, O. Chételat, C. Sartori, and S. F. Rimoldi, "Parametric estimation of pulse arrival time: a robust approach to pulse wave velocity," *Physiol. Meas.*, vol. 30, pp. 603-615, 2009 (Ref. 2), a parametric approach to estimate PAT in low SNR conditions is described. Instead of identifying a characteristic point in a PPG pressure pulse this approach fits a parametric model onto the entire pulse. A PAT-equivalent value is finally extracted from the parameters of the model.

Figure 2:
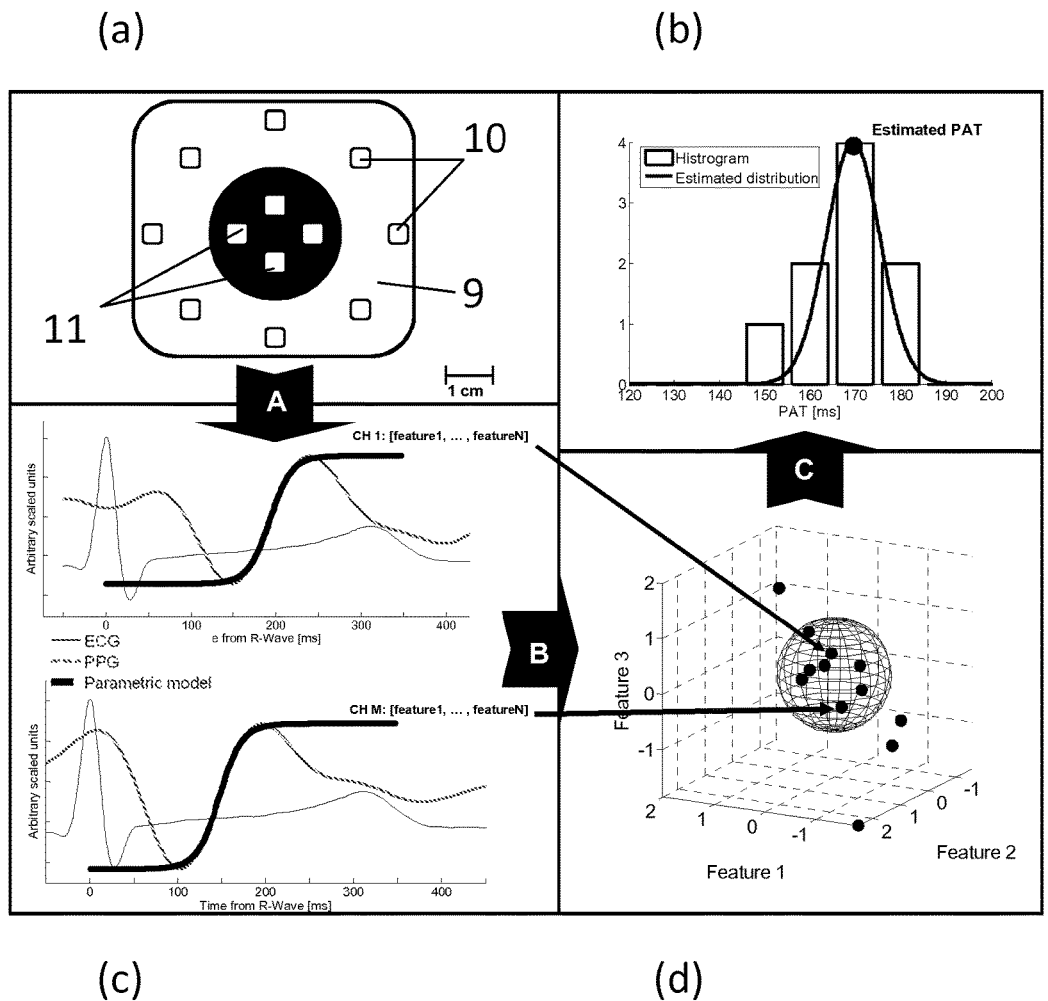
FIG. 2 shows a PPG multichannel sensor according to an embodiment and two examples of shape and arrival times of pressure pulses seen by the PPG multichannel sensor.

A proposed method for measuring and determining the PAT value combines thus the parametric information extracted from a set of M simultaneously-recorded PPG channels of the PPG multichannel sensor 9, and provides a single robust estimation of PAT. For example, the method comprises three steps, as illustrated by FIG. 2. More particularly, FIG. 2(a) shows the PPG multichannel sensor 9 intended to be placed on the skin (for example of the chest) of a user and formed from a plurality of PPG sensor channels, according to an embodiment. Each PPG sensor channel is formed from an emitter 10 comprising a first radiation source emitting at the infrared wavelengths, and a receiver 11, such as a photodetector, for receiving the optical radiation emitted by the emitter 10 and transmitted through the skin tissue. The receiver 11 is connected to an analog-to-digital converter ADC module (not represented) delivering corresponding PPG signals. In the example of FIG. 2(*a*), the multichannel sensor 9 contains eight equally radially distributed channels. Other arrangements of the emitters 10 and receivers 11 are also possible as long as it provides sufficient spatial diversity in order to remove artifacts due to tissue inhomogeneities. Spatial diversity allows one to remove measurement noise as well as reduce artifacts related to movements which may not be recorded by an accelerometer. However, this requires a more sophisticated control and signal processing.

First, a parametric model is estimated for each of the M PPG channels. The shape and arrival time of the pressure pulse seen by each channel is described by N parameters (see the two graphs below the PPG multichannel sensor 9 in FIG. 2(*b*)), which correspond to a point in an N-dimensional feature space. Secondly, the distribution of the M points in this feature space is considered: outsiders are removed by an unsupervised clustering procedure described in V. J. Hodge and J. Austin, "A Survey of Outlier Detection Methodologies," *Artificial Intelligence Review*, Springer, 2004, in order to estimate the most likely model of pressure pulse. The clustering procedure aims at excluding non-representative (probably low-perfused) channels from the analysis. The procedure relies on the assumption that whereas those PPG channels located over a locally rich capillary bed generate similar parametric descriptions, those PPG channels located over low-perfused regions generate spread points in the feature space. Thus, non-representative channels are defined as points that lay beyond the borders of a hypersphere in a Mahalanobis-transformed feature space (see FIG. 2(*c*)). Thirdly, the parametric descriptions of the remaining representative channels are processed through a histogram analysis to provide a single PAT value (see FIG. 2(*d*)).

In an embodiment, the method for measuring and determining the PAT value comprises the steps of:

measuring a set of PPG signals using the PPG multichannel sensor, where the set of PPG signals contains a number of PPG signals corresponding to the number of PPG sensor channels;

extracting a plurality of features from each of the measured PPG signals;

selecting a subset from the set of PPG signals based on the extracted features; and processing the selected subset of PPG signals to determine the PAT value.

In an embodiment, the plurality of features is extracted by fitting a parametric model to each PPG signal of said set of PPG signals, the features corresponding to the parameters of the fitted model. The parametric model can be TANH model, as discussed below.

Because phase velocity information of pressure pulses is mainly contained in high frequencies harmonics, PPG channels can be initially high-pass filtered without any loss of relevant information. In addition to increase the signal-to-noise ratio, high-pass filtering limits as well non-relevant channel-dependent patterns that might latter influence the parametric model fitting.

The joint analysis of the ECG, PCG, ICG and PPG signals recorded at the sensor device 4 provides information on the opening of the aortic valve (PEP), and the arrival time of the pressure pulse (PAT), for example, at the chest. Then, a Pulse Transit Time value (PTT) from the aortic valve to, for example, the chest is obtained as the difference (Equation 1):

$$PTT = PAT - PEP \qquad \text{(Equation 1)}.$$

However, because the clinical interest of pressure pulse propagation is on the assessment of propagation velocities (m/s) and not on propagation times (ms), PTT values estimated form the signals measured with the sensor device 4 placed on the user's chest (Chest PTT values) in ms, can be converted into chest PWV values, in m/s. In principle such a transformation would require the accurate measurement of propagation distances within the chest, which is not straightforward in a non-invasive manner.

Based on the propagation distances measured during standard COMPLIOR uses (see: M. W. Rajzer, W. Wojciechowska, M. Klocek, I. Palka, M. Brzozowska-Kiska, and K. Kawecka-Jaszcz, "Comparison of aortic pulse wave velocity measured by three techniques: Complior, SphygmoCor and Arteriograph," *J. Hypertension*, vol. 26, pp. 2001-2007, 2008), the following conversion model is proposed. The propagation distance from the aortic valve to the upper sternum region is approximated by the COMPLIOR carotid to radial distance corrected by the ratio of carotid to femoral over carotid to radial COMPLIOR distances. The proposed correction factor is actually an estimate of the ratio of elastic-over-muscular arterial segments present in the COMPLIOR carotid to radial PWV value. FIG. 3(*a*) illustrates a preferred embodiment where the PPG multichannel sensor 9 is placed on the chest of the user in contact with the skin via the belt 7. The belt also comprises the ICG and PCG sensors 5, 6. Also shown in FIG. 3(*b*) is a schematic representation of the successive determination of the PEP and PAT values from which the chest PTT and chest PWV values are estimated. The sensor device 4 can also comprise a signal processing device (not shown) destined to receive the sensor signals and to carry out the method for estimating the PTT and PWV values as described above. In the right of FIG. 3(*b*), a diagram shows the signals from the PCG and ICG sensors being combined to detect the opening of the aortic valve, producing the pre-ejection period (PEP) value. The PPG multichannel sensor provides an estimation on the arrival time of the pressure pulse at the capillary bed at the sternum (PAT). The pulse transit time (PTT) from the aortic valve to the chest is computed by subtracting PEP from PAT. Pulse wave velocity (PWV) is finally estimated by converting PTT values (in ms) to PWV values (in m/s).

Our investigation was based on a training-testing study approach. Initially, a training study involving eight healthy subjects was performed. This study aimed at optimizing the parameters of the sensor device 4, comprising the ICG and PCG sensors 5, 6 the PPG multichannel sensor 9, and possibly the ECG sensor 12, in order to maximize the correlation between estimated chest PWV values and simultaneously-recorded COMPLIOR carotid to radial PWV values. In a second step, a testing study involving twenty one healthy subjects was performed. This study aimed at testing the performances of the sensor device 4 when predicting COMPLIOR PWV values on a different cohort.

For both studies, the experimental protocol was approved by the institutional review boards on human investigation of the University of Lausanne, Switzerland. All participants provided written informed consent.

The experimental protocol consisted on the simultaneous recording of both COMPLIOR and chest PWV values at rest. After enrollment, subjects laid in supine position while two operators started the instrumentation phase. Measurements with the sensor device 4 were performed by means of the PPG multichannel sensor 9 and two spot wet ECG electrodes, (1 kSample/s) and a BIOPAC (BIOPAC Systems, US) platform (4 spot wet electrodes connected to an EBI100C electrical bio-impedance amplifier, 50 kHz, 1 kSample/s; and 2 spot wet electrodes connected to an ECG100C electrocardiogram amplifier, 1 kSample/s). The placement of the sensor device 4 on the chest and/or sternum set a constant temperature of the sensor measurement surface, reducing temperature-induced skin vasocontraction phenomena. The set of PPG signals was measured continuously by the PPG multichannel sensor 9 along with the ICG signals measured by the ICG sensor 5, ECG signals measured by the ECG sensor 12 and PCG signals measured by the PCG sensor 6. Measurements were performed in a fully unsupervised manner during the whole experiment. COMPLIOR PWV measurements were performed according to standard COMPLIOR uses, i.e., after measuring external carotid to femoral and carotid to radial distances, three pressure transducers were placed over the carotid, femoral and radial arteries. A skilled operator visualized the quality of the data in real time and decided when a measurement could be performed. Consecutive COMPLIOR measurements were performed until a set of at least three similar COMPLIOR PWV values were available. Brachial oscillometric blood pressure was measured as well. Finally, subjects were cleared and data sets were stored for off-line data analysis.

Figure 4:
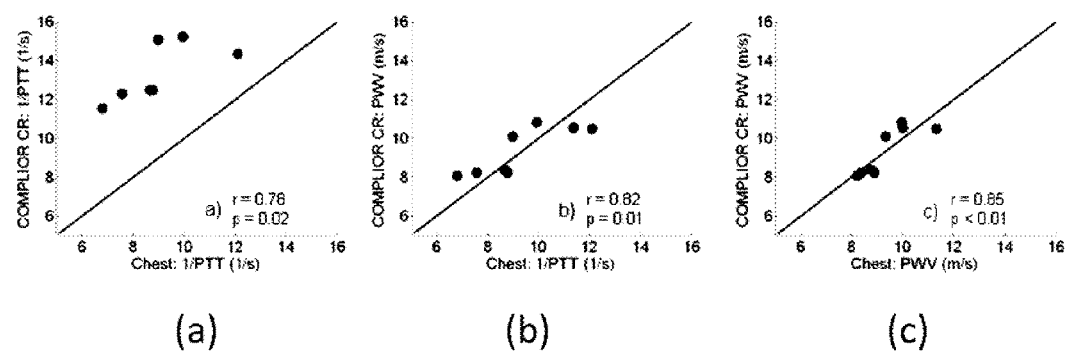
FIG. 4 shows correlation plots of 1/PTT values provided by the chest sensor and the COMPLIOR carotid.

A preliminary study involving eight subjects (Age: 26 to 41 years, BMI: 19 to 23 kg/m$^2$, COMPLIOR CR PWV 8 to10.8 m/s) was performed in order to optimize the algorithms of the sensor device 4. In particular, the training study allowed parametrizing the detector of aortic valve opening (see FIG. 1(b)), the chest PAT detector (see FIG. 2(b)), and the conversion of chest PTT values to COMPLIOR equivalent PWV values (FIG. 4). Offline recursive optimization was performed until achievement of optimal correlation between chest PWV values and COMPLIOR carotid to radial PWV values. The choice of carotid to radial PWV as reference values is justified by the anatomical study provided above. The following parameterization was obtained.

ICG signals were initially band-pass filtered by a 4$^{th}$ order Butterworth filter with cut-off frequencies of 0.8 and 15 Hz. Third derivatives were computed by applying successive seven-point stencils. PCG envelopes were computed by initially band-pass filtering the raw PCG data by a 4$^{th}$ order Butterworth filter with cut-off frequencies of 50 and 140 Hz, and by post filtering the absolute value of the band-pass filtered series with a 4$^{th}$ order Butterworth low-pass filter with cut-off frequency of 10 Hz. Finally, two-minute signals of ICG and PCG were ensemble averaged using the R-Wave of the simultaneously-recorded ECG signal as synchronization trigger. The most likely maximum of the ensemble averaged third derivatives was manually identified by finding the local maximum closer to the maximum of the ensemble averaged PCG envelope (PCG-guided B-point identification).

Before being oversampled to 1 kSample/s, each infrared PPG channel was band-pass filtered by an 8$^{th}$ order Butterworth filter with cut-off frequencies between 3 and 9 Hz. After performing a two-minute R-Wave-triggered ensemble averaging, a parametric model of the pressure pulse was fitted according to a parametric model, for example a TANH model, as described in Ref. 2. The parameters of the model were then considered in a 3-dimensional feature space, where unsupervised outlier rejection was performed. For each channel, Mahalanobis distance of the associated point to the median of all available points was computed. Those channels with greater distances than the standard deviation of all the distances were rejected. From the remaining representative channels, the mean of individuals PAT values was assumed to be the most likely PAT at the chest.

In an embodiment, in the method for measuring and determining the PAT value, selecting the subset of PPG signals comprises projecting the features extracted from each of the measured PPG signal into a set of points in a N-dimensional feature space where N corresponds to the number of extracted features for each PPG signal; clustering the set of points according to a distance criterion; and selecting points being located at the most representative cluster, the selected points corresponding to the subset of PPG signals. The clustering the set of points can be performed by calculating a representative point; calculating a distance for the set of points to the representative point; and clustering together those points being located at a distance smaller than a distance threshold. Calculating the representative point comprises calculating the median point of the set of points, and calculating the distance for the set of points comprises calculating a Mahalanobis distance as described above.

The distance threshold can be calculated from a histogram of the distances for the set of points to the representative point. Processing the selected subset of PPG signals can be performed by estimating the mean value of the selected subset of PPG signals. Alternatively, processing the selected subset of PPG signals comprises estimating a representative value of at least one of the features extracted from each of the selected subset of PPG signals.

In another embodiment, the PWV value is used to calculate continuous, non-invasive and non-obtrusive blood pressure (BP) values of a user (see Ref. 1). The BP values can be derived from PWV values using a method described in Chen, W.; Kobayashi, T.; Ichikawa, S.; Takeuchi, Y. & Togawa, T. (2000). Continuous estimation of systolic blood pressure using the pulse arrival time and intermittent calibration. *Medical & Biological Engineering & Computing*, 38, (2000) 569-574. This method comprises measuring reference BP values using a brachial cuff, where brachial cuff can be automatic and intermittently inflated. In the method, PWV values are calibrated according to measured reference BP values, and calibrated PWV values are used to interpolate the intermittently measured BP values, for example, beat by beat. Additional calibration strategies to calculate PWV-derived values of BP are also reviewed in Ref. 1. In particular, patent application US 2009/0163821 describes a method to improve the accuracy of PWV-derived BP calculations by introducing a cardiac output measurement. BP measurements are performed by an oscillometric brachial cuff. Cardiac output measurements can be performed by bio-impedance techniques.

Alternatively, a blood pressure value can calculated be from the estimated PTT value by measuring reference blood pressure values using a brachial cuff, and calibrating PTT values according to measured reference blood pressure values. Hence, blood pressure value can be calculated in a continuous, non-invasive and non-obtrusive fashion.

FIG. 4 illustrates the impact of converting chest PTT to chest PWV values in the optimization of correlation analysis scores. Initially, transit times (PTT) estimated by the sensor device 4 and COMPLIOR were compared. Since no propagation distance was involved in the analysis, moderate correlation scores were obtained: r=0.78, p=0.02. Propagation distances for the COMPLIOR measurement were then introduced, converting COMPLIOR PTT values to COMPLIOR PWV values. An improvement of the correlation score was observed (r=0.82, p=0.01). In a last step, propagation distances for the sensor device were introduced, converting Chest PTT values to Chest PWV values. A final correlation score of r=0.85, p<0.01 was achieved. A regression line between COMPLIOR PWV and Chest PWV values was estimated as well. While keeping the same correlation scores, this procedure minimized the root mean square error when comparing Chest PWV values to COMPLIOR PWV values for this training cohort.

More particularly, FIG. 4 shows a correlation plot of 1/PTT values provided by the sensor device and the COMPLIOR carotid to radial setup (FIG. 4(a)); a correlation of 1/PTT values provided by the sensor device and PWV values provided by the COMPLIOR carotid to radial setup (COMPLIOR carotid to radial distance has been introduced) (FIG. 4(b)); and a correlation of PWV values provided by the sensor device and the COMPLIOR carotid to radial setup (chest propagation distance has been introduced, as described above (FIG. 4(c)).

Figure 5:
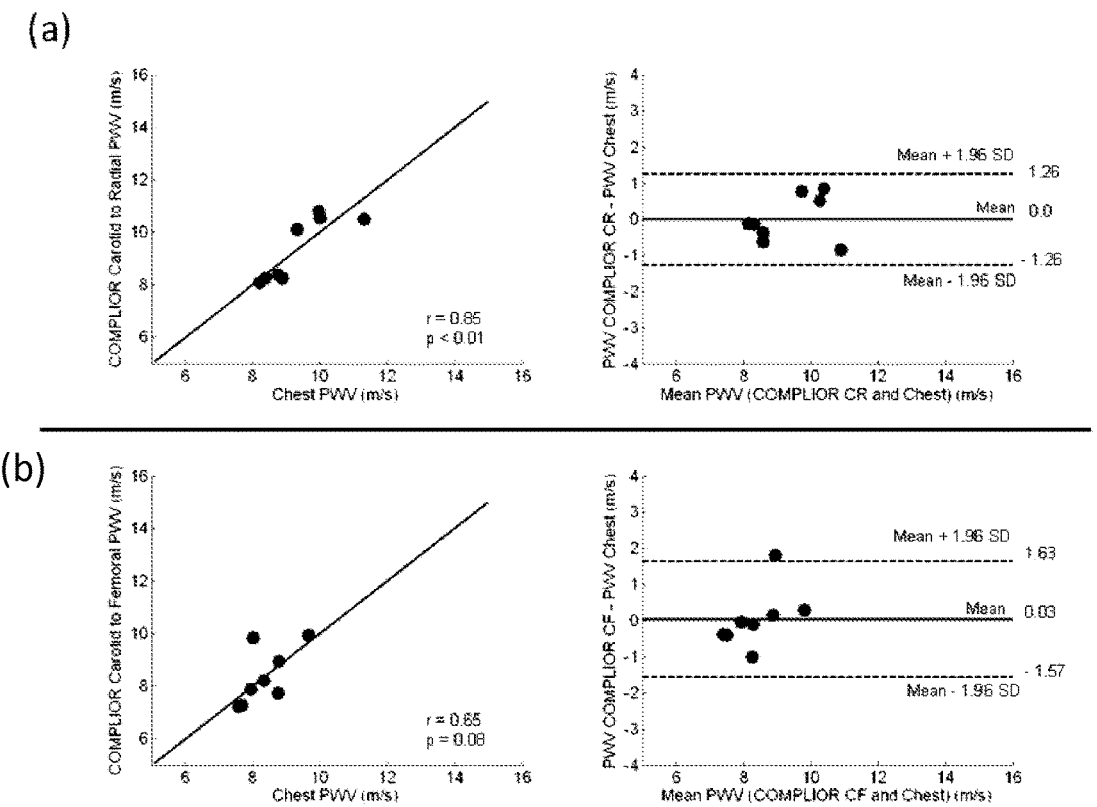
FIG. 5 illustrates correlation analysis and Bland-Altman plots for a preliminary training study with eight subjects.

Table 1 provides correlation coefficients, Root Mean Square Error (RMSE) and mean bias when comparing PWV values determined from the sensor device 4 to PWV values measured by COMPLIOR carotid to radial and carotid to femoral sensors. FIG. 5 illustrates correlation analysis and Bland-Altman plots for the same data set, when comparing chest PWV measurements to COMPLIOR Carotid to Radial (CR) (FIG. 5(a)) and Carotid to Femoral (CF) (FIG. 5(b)) measurements for the preliminary training study (n=8 subjects). As expected, the maximum correlation score (r=0.86) and minimum RMSE (RMSE=0.65 m/s) were achieved when comparing Chest PWV values to COMPLIOR carotid to radial PWV values, since this was the algorithm optimization criterion. Zero mean biases were due to the fact that regression lines were self-estimated over the same training data set.

After optimizing the sensor device on the training preliminary study, the performance of the sensor was assessed in a control group study.

TABLE I

Statistical analysis for the preliminary training study (n = 8)

| Chest PWV compared to | Carotid to Radial PWV | Carotid to Femoral PWV |
|---|---|---|
| Correlation coefficient | r = 0.85 p < 0.01 | r = 0.65 p = 0.08 |
| Root mean square error (RMSE) | 0.65 m/s | 0.81 m/s |
| Mean Bias | 0.0 m/s | 0.0 m/s |

The validation study was designed to provide a statistically significant answer on whether PWV values provided by the sensor device correlate and predict PWV values estimated by a COMPLIOR device within a 1 m/s error. Minimum sample size for the study was estimated according to training database statistics ($\sigma_{CHEST}^2$=1.22 m/s and $\sigma_{COMPLIOR}^2$=1.07 m/s), and assuming a two-sided alternate hypothesis, i.e., $|\mu_{CHEST}-\mu_{COMPLIOR}|<1$ m/s. By choosing power values of $\alpha$=5% and $\beta$=20% a minimum sample size of 20.4 subjects was obtained.

According to the power analysis, the validation study started by the recruitment of twenty one subjects. Table 2 summarizes the morphological and hemodynamic characteristics for the enrolled subjects. The same experimental protocol as for the preliminary training study was performed. Data analysis was performed offline once the entire validation database had been recorded. The algorithmic parameterization corresponded to the one derived from the preliminary training study, as described above. Chest PWV values were compared to COMPLIOR carotid to radial and carotid to femoral PWV values, using correlation analysis, Root Mean Square Error (RMSE) analysis, bias analysis and Bland-Altman plot.

TABLE II

Morphological and hemodynamic characteristics of the validation study population (n = 21)

| Symbol | Mean ± SD | Min . . . Max |
|---|---|---|
| Age (years) | 41 ± 11.7 | 26 to 61 |
| BMI (kg/m$^2$) | 25 ± 4.3 | 19.4 to 40.4 |
| Heart Rate (bpm) | 62 ± 7.2 | 50 to 76 |
| Systolic Blood Pressure (mmHg) | 126 ± 11.8 | 105 to 143 |
| Diastolic Blood Pressure (mmHg) | 77 ± 8.2 | 55 to 94 |
| Pulse Wave Velocity | | |
| Complior Carotid - Femoral (m/s) | 9 ± 1.7 | 6.2 to 14.7 |
| Complior Carotid - Radial (m/s) | 10 ± 1.1 | 8.3 to 12.3 |

Figure 6:
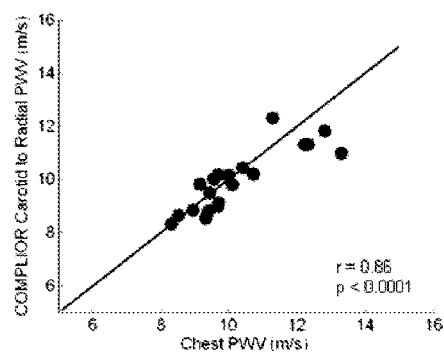
FIG. 6 illustrates correlation analysis and Bland-Altman plots for a validation study with twenty subjects.
Figure 6:
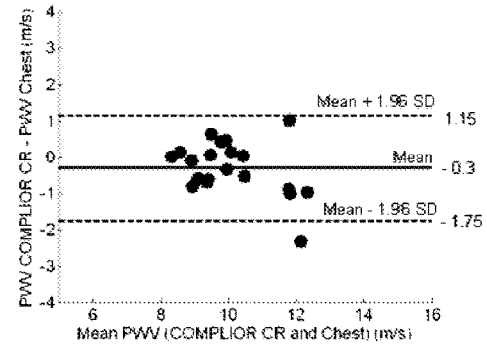
Figure 6:
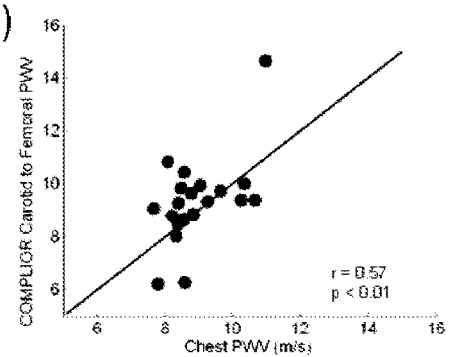
Figure 6:
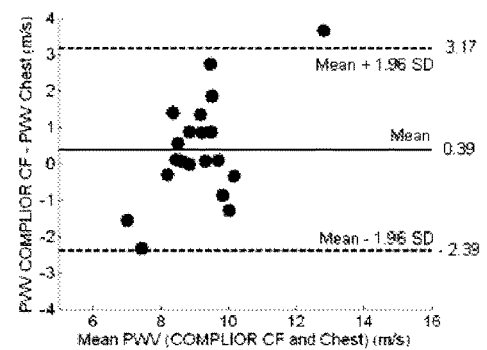

From the twenty one subjects enrolled in the validation study, one was excluded because the COMPLIOR device was unable to detect carotid pressure pulses. Hence, the results of the validation study correspond to the analysis of the data recorded from 20 subjects when using the parameterization derived from the preliminary training study. Table III provides the statistical analysis, and FIG. 6 illustrates the correlation analysis and Bland-Altman plots when comparing chest PWV measurements to COMPLIOR Carotid to Radial (CR) (FIG. 6(a)) and Carotid to Femoral (CF) (FIG. 6(b)) measurements for the data recorded from 20 subjects.

When comparing chest PWV values to COMPLIOR carotid to radial values for this testing cohort, one observes that the sensor device provides similar correlation scores as obtained for the training cohort (achieved correlation in training of r=0.85, p<0.01 vs. observed correlation in testing r=0.86, p<0.0001). Similarly, RMSE values remain in the same range of values (training RMSE 0.65 m/s vs. testing RMSE 0.74 m/s). These results indicate that the algorithmic parameterization and the regression line estimated on the training cohort apply as well for this unknown testing cohort. The mean bias slightly differs now from zero (mean bias −0.3 m/s). One single subject depicts a prediction error greater than 1.96 SD in the Bland-Altman plot (COMPLIOR CR 13.3 m/s, Chest PWV 11.0 m/s).

TABLE III

Statistical analysis for the preliminary training study (n = 20)

| Chest PWV compared to | Carotid to Radial PWV | Carotid to Femoral PWV |
|---|---|---|
| Correlation coefficient | r = 0.86 p < 0.0001 | r = 0.57 p = 0.01 |
| Root mean square error (RMSE) | 0.74 m/s | 1.42 m/s |
| Mean Bias | −0.3 m/s | 0.39 m/s |

When comparing chest PWV values to COMPLIOR carotid to femoral values, one observes that both correlation and RMSE performances are degraded compared to the training study: correlation in training r=0.65, p=0.08 vs. correlation in testing r=0.57, p<0.01, and RMSE in training 0.81 m/s vs. RMSE in testing 1.42 m/s. Several outlier subjects are now observed in the Bland-Altman plot.

This study aimed at demonstrating that a non-obtrusive sensor located at the chest region is able to measure central PWV in a fully unsupervised and unobtrusive manner. The major new finding of our study is that Chest PWV correlates very well with COMPLIOR carotid to radial PWV ($r=0.86$, $p<0.0001$) and only well with COMPLIOR carotid to femoral PWV ($r=0.57$, $p<0.01$). Because of the study design, the RMSE analysis confirms that Chest PWV predicts the COMPLIOR carotid to radial PWV within a $\pm 1$ m/s error (RMSE=0.74 m/s).

In accordance with an aspect of the invention, there is provided a computer program product configured to be operable on the signal processing device in order to carry out the processing of the sensor signals to determine the PTT and PWV values. The processing is performed according to the method described above when the program is executed by said signal processing device. The software product can be downloaded in a memory (not shown) associated with the signal processing device.

REFERENCE NUMBERS 4 sensor device
5 ICG sensor
6 PCG sensor
7 belt
8 user
9 PPG multichannel sensor
10 emitter
11 receiver
12 ECG sensor
S1 envelope

The invention claimed is:

1. A method for measuring and determining a single pulse arrival time (PAT) value at a given location of a user, wherein the PAT value is the time for a pulse to arrive at said location following a contraction of the heart of the user, using a sensor device comprising a photoplethysmographic (PPG) multichannel sensor formed from a plurality of PPG sensor channels and being adapted to measure a set of PPG signals, each PPG signal being measured by one of the PPG sensor channels when the multichannel PPG sensor is in contact with the user; comprising:
    measuring noninvasively said set of PPG signals;
    extracting a plurality of features from each of the measured PPG signals;
    selecting a subset from the set of PPG signals based on the extracted features; and
    processing the selected subset of PPG signals to noninvasively determine the PAT value,
    wherein said selecting the subset of PPG signals comprises:
        projecting the plurality of features extracted from each of the measured PPG signal into a set of points in a N-dimensional feature space where N corresponds to the number of extracted features for each PPG signal;
        clustering the set of points according to a distance criterion; and
        selecting points being located at a representative cluster, the selected points corresponding to the subset of PPG signals.

2. The method according to claim 1, wherein said extracting the plurality of features comprises fitting a parametric model to each PPG signal of said set of PPG signals, the features corresponding to the parameters of the fitted model.

3. The method according to claim 1, wherein said processing the selected subset of PPG signals comprises estimating a representative value of at least one of the features extracted from each of the selected subset of PPG signals.

4. The method according to claim 1, wherein said clustering the set of points comprises:
    calculating a representative point;
    calculating a distance for the set of points to the representative point; and
    clustering together those points being located at a distance smaller than a distance threshold.

5. The method according to claim 4, wherein said calculating the representative point comprises calculating the median point of the set of points.

6. The method according to claim 4, wherein said calculating the distance for the set of points comprises calculating a Mahalanobis distance.

7. The method according to claim 4, wherein said distance threshold is calculated from a histogram of the distances for the set of points to the representative point.

8. The method according to claim 1, wherein the sensor device further comprises an electrocardiography (ECG) sensor for measuring an ECG signal, an impedance cardiography (ICG) sensor for measuring an ICG signal, and a phonocardiography (PCG) sensor for measuring a PCG signal; further comprising:
    measuring the ECG signal with the ECG sensor such as to detect a R-Wave corresponding to the onset of left-ventricular depolarization,
    triggering the PCG signal measured by the PCG sensor and the ICG signal measured by the ICG sensor by the detected R-Wave;
    performing an ensemble average of the triggered PCG signal and ICG signal;
    calculating the maximum of the envelope of the ensemble-averaged PCG signal; and
    detecting a maximum of the third derivative of the ensemble-averaged ICG signal being closest to the maximum of the envelope such as to determine a value of a pre-ejection period (PEP).

9. The method according to claim 8, wherein the determined value of the pre-ejection period (PEP) is being used in combination with the determined PAT value to estimate a pulse transit time (PTT) value.

10. The method according to claim 9, further comprising calculating a blood pressure value from the estimated PTT value by measuring reference blood pressure values using a brachial cuff, and calibrating PTT values according to measured reference blood pressure values.

11. The method according to claim 9, wherein further comprising estimating a pulse wave velocity (PWV) value by dividing the estimated PTT value by a measured distance of the user's body.

12. The method according to claim 11, further comprising calculating a blood pressure value from the estimated PWV value by measuring reference blood pressure values using a brachial cuff, and calibrating PWV values according to measured reference blood pressure values.

13. A sensor device for measuring and determining noninvasively a pulse arrival time (PAT) value at a given location of a user, wherein the PAT value is the time for a pulse to arrive at said location following a contraction of the heart of the user, the sensor device comprising a photoplethysmographic (PPG) multichannel sensor formed from a plurality of PPG sensor channels and being adapted to measure a set of PPG signals, each PPG signal being measured by one of the PPG sensor channels when the multichannel PPG sensor is in contact with the user, wherein the sensor device is configured to determine the PAT value by:
  measuring noninvasively said set of PPG signals;
  extracting a plurality of features from each of the measured PPG signals;
  selecting a subset from the set of PPG signals based on the extracted features; and
  processing the selected subset of PPG signals to noninvasively determine the PAT value,
  wherein said selecting the subset of PPG signals comprises:
    projecting the plurality of features extracted from each of the measured PPG signal into a set of points in a N-dimensional feature space where N corresponds to the number of extracted features for each PPG signal;
    clustering the set of points according to a distance criterion; and
    selecting points being located at a representative cluster, the selected points corresponding to the subset of PPG signals.

14. The sensor device according to claim 13, further comprising an impedance cardiography (ICG) sensor for measuring an ICG signal, an electrocardiography (ECG) sensor for measuring an ECG signal, and a phonocardiography (PCG) sensor for measuring a PCG signal; the ICG sensor, ECG sensor, and PCG sensor being used in combination for determining a value of a pre-ejection period (PEP).

15. The sensor device according to claim 14, wherein the sensor device is further configured to determine the value of the PEP by:
  measuring the ECG signal with the ECG sensor such as to detect a R-Wave corresponding to the onset of left-ventricular depolarization,
  triggering the PCG signal measured by the PCG sensor and the ICG signal measured by the ICG sensor by the detected R-Wave;
  performing an ensemble average of the triggered PCG signal and ICG signal;
  calculating the maximum of the envelope of the ensemble-averaged PCG signal; and
  detecting a maximum of the third derivative of the ensemble-averaged ICG signal being closest to the maximum of the envelope such as to determine the value of PEP.

16. A non-transitory computer readable medium comprising program code portions to be executed by a signal processing device in order to carry out a method for measuring and determining noninvasively a single pulse arrival time (PAT) value of a user, wherein the PAT value is the time for a pulse to arrive at a given location following a contraction of the heart of the user, using a sensor device comprising a photoplethysmographic (PPG) multichannel sensor formed from a plurality of PPG sensor channels and being adapted to measure a set of PPG signals, each PPG signal being measured by one of the PPG sensor channels when the multichannel PPG sensor is in contact with the user; the method comprising:
  measuring noninvasively said set of PPG signals;
  extracting a plurality of features from each of the measured PPG signals;
  selecting a subset from the set of PPG signals based on the extracted features; and
  processing the selected subset of PPG signals to noninvasively determine the PAT value;
when said program is executed by said signal processing device,
  wherein said selecting the subset of PPG signals comprises:
    projecting the plurality of features extracted from each of the measured PPG signal into a set of points in a N-dimensional feature space where N corresponds to the number of extracted features for each PPG signal;
    clustering the set of points according to a distance criterion; and
    selecting points being located at a representative cluster, the selected points corresponding to the subset of PPG signals.

* * * * *